United States Patent
Sepetka et al.

(10) Patent No.: US 10,342,546 B2
(45) Date of Patent: Jul. 9, 2019

(54) OCCLUSIVE DEVICE

(71) Applicant: MicroVention, Inc., Aliso Viejo, CA (US)

(72) Inventors: Ivan Sepetka, Los Altos, CA (US); Cathy Lei, Chino Hills, CA (US); Matthew Fitz, Vista, CA (US)

(73) Assignee: MicroVention, Inc., Tustin, CA (US)

( * ) Notice: Subject to any disclaimer, the term of this patent is extended or adjusted under 35 U.S.C. 154(b) by 512 days.

(21) Appl. No.: 13/831,516

(22) Filed: Mar. 14, 2013

(65) Prior Publication Data

US 2014/0200607 A1 Jul. 17, 2014

Related U.S. Application Data

(60) Provisional application No. 61/752,373, filed on Jan. 14, 2013.

(51) Int. Cl.
*A61B 17/12* (2006.01)
*A61B 17/00* (2006.01)

(52) U.S. Cl.
CPC .... *A61B 17/12109* (2013.01); *A61B 17/1214* (2013.01); *A61B 17/12031* (2013.01); *A61B 17/12113* (2013.01); *A61B 17/12172* (2013.01); *A61B 2017/00867* (2013.01); *A61B 2017/12054* (2013.01); *A61B 2017/12063* (2013.01); *A61B 2017/12068* (2013.01)

(58) Field of Classification Search
CPC ........ A61B 17/12109; A61B 17/12031; A61B 17/1214; A61B 17/12113; A61B 17/12172; A61B 17/12; A61B 17/12177; A61B 17/12022; A61M 25/10

USPC .......................................................... 606/200
See application file for complete search history.

(56) References Cited

U.S. PATENT DOCUMENTS

| | | | |
|---|---|---|---|
| 6,391,037 B1 | 5/2002 | Greenhalgh | |
| 6,592,617 B2 * | 7/2003 | Thompson | ................ A61F 2/90 623/1.53 |
| 2002/0143348 A1 | 10/2002 | Wallace et al. | |
| 2002/0177855 A1 | 11/2002 | Green, Jr. et al. | |
| 2003/0028209 A1 | 2/2003 | Teoh et al. | |
| 2007/0288040 A1 * | 12/2007 | Ferree | ..................... A61F 2/442 606/151 |
| 2008/0281350 A1 * | 11/2008 | Sepetka | ............. A61B 17/0057 606/200 |
| 2010/0268204 A1 | 10/2010 | Tieu et al. | |
| 2010/0324649 A1 * | 12/2010 | Mattsson | .................. A61F 2/07 623/1.12 |
| 2011/0152993 A1 | 7/2011 | Marchand et al. | |

(Continued)

FOREIGN PATENT DOCUMENTS

WO WO 02/069783 A2 9/2002
WO WO2013074486 A1 5/2013

OTHER PUBLICATIONS

WIPO, U.S. International Searching Authority, International Search Report and Written Opinion dated Mar. 21, 2014 in International Patent Application No. PCT/US2014/011522, 11 pages.

*Primary Examiner* — Christopher L Templeton
*Assistant Examiner* — George J Ulsh
(74) *Attorney, Agent, or Firm* — Inskeep IP Group, Inc.

(57) ABSTRACT

An occlusive device comprising a braided component which can be inserted into a blood vessel and a delivery system for delivering said occlusive device is described.

16 Claims, 21 Drawing Sheets

(56) References Cited

U.S. PATENT DOCUMENTS

2012/0245674 A1    9/2012   Molaei et al.
2012/0283768 A1   11/2012   Cox et al.
2013/0116722 A1*   5/2013   Aboytes ................ A61M 29/00
                                                                               606/198
2014/0135812 A1*   5/2014   Divino ............. A61B 17/12113
                                                                               606/194

\* cited by examiner

OCCLUSIVE DEVICE

RELATED APPLICATIONS

This application claims priority to U.S. Provisional Application Ser. No. 61/752,373 filed Jan. 14, 2013 entitled Occlusive Device, which is hereby incorporated herein by reference in its entirety.

BACKGROUND OF THE INVENTION

Occlusive devices, such as coils and plugs, are often used to treat various intravascular conditions such as arteriovenous malformation (AVM), aneurysm, fistula, atrial septal defect, patent foramen ovale, left atrial appendage, and other general blood vessel malformations. These devices occlude the cavity and limit blood flow to the malformation to reduce the chance of any bursting of the blood vessel. These devices must be able to effectively occlude all the space in order to prevent blood flow into the vessel malformation, and allow the malformation to clot. The use of an occlusive device with a flexible, conforming shape would be beneficial in order to effectively fill the space in a malformation.

SUMMARY OF THE INVENTION

An occlusive device and a delivery system for delivering said occlusive device is described.

Generally, the occlusive device has a distal portion configured to conform to an interior surface of a vascular malformation; and a proximal portion configured to substantially fill a remaining interior volume of the vascular malformation after the distal portion is deployed therein.

In one embodiment the occlusive device is a straight tubular braid that makes up both the distal portion and the proximal portion.

In another embodiment the occlusive device is a linearly tapered tubular braid.

In another embodiment the occlusive device is a step-tapered tubular braid.

In another embodiment the occlusive device is a braid with a trumpeted shape at one end.

In another embodiment the occlusive device is a braid with a trumpeted shape at both ends.

In another embodiment the occlusive device is a braid with a variable pitch.

In another embodiment the occlusive device is a braided structure connected to a coil-shaped structure such that the braided structure makes up the distal portion and the coil-shaped structure makes up the proximal portion, or vice versa.

In another embodiment the occlusive device is a braid segmented by radiopaque markers to create a variable diameter shape.

In another embodiment the occlusive device is a braid which is electropolished at various areas along its length to provide variable wall thickness.

In another embodiment the occlusive device is a braid connected to one or more coils such that the braid makes up the distal portion and the coils make up the proximal portion, or vice versa.

In another embodiment the occlusive device is a braid connected to one or more embolic coils.

In one embodiment, a delivery system is provided that includes a sheath and a pusher slidably disposed within the sheath.

In one embodiment a delivery system for delivering an occlusive device includes a core wire pusher.

In another embodiment a delivery system for delivering an occlusive device includes an elastic pusher.

In another embodiment a delivery system for delivering an occlusive device includes a hypotube pusher.

In one embodiment an occlusive device is connected to a pusher and said occlusive device is delivered in a linear configuration.

In another embodiment an occlusive device is connected to a pusher and said occlusive device is delivered in an inverted configuration.

In another embodiment an occlusive device is connected to a pusher at multiple points along said pusher and said occlusive device is delivered in an inverted configuration.

In another embodiment an occlusive device is connected to a pusher at multiple points along said pusher and said occlusive device is delivered in a linear configuration.

One aspect of the invention is a method of occluding a vascular malformation including pushing a distal portion of an occlusive device through a distal end of a delivery device into a vascular malformation, allowing the distal portion to expand and adapt to a shape of the vascular malformation, and pushing a proximal portion of the occlusive device through the distal end of said delivery device into a space remaining within said distal portion to fill a remaining space inside said vascular malformation.

BRIEF DESCRIPTION OF THE DRAWINGS

These and other aspects, features and advantages of the invention will be apparent and elucidated from the following description of embodiments of the present invention, reference being made to the accompanying drawings, in which.

DESCRIPTION OF EMBODIMENTS

Figure 1:
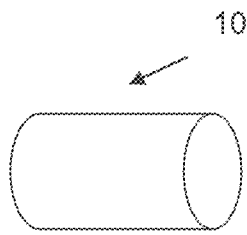
FIG. 1 illustrates a straight tubular braided occlusive device.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The term aneurysm may be used to describe a particular vessel abnormality or malformation, however, this term is not meant to be overly limiting to solely aneurysms. The device described may be used to treat—for example—aneurysms, fistulas, septal defects, left atrial appendages, arteriovenous malformations, patent foramen ovale, and other general vessel malformations and should be construed as being applied to a general swath of blood vessel malformations which may occur within the vascular system.

The various occlusive devices described herein generally have a distal portion and a proximal portion. The distal portion is deemed to be that portion of the device that is delivered first and conforms to an interior surface of the vascular malformation. The proximal portion is deemed to be that portion of the device that is delivered after the distal portion has been delivered.

The distinction between the distal portion and the proximal portions, for many embodiments, will be determined by the size and shape of the targeted malformation. For example, in the case of a tubular braided device, the device will tend to expand radially until the walls of the device come into contact with the walls of the malformation, additional material delivered to the malformation will cause a fold near the opening of the malformation and the additional braided material will fold itself into the distal portion of the braid that is in contact with the walls of the malformation.

In other embodiments, which feature two different structures, the distal and proximal portions may be distinguished by the structures themselves. For example, in the case of a tubular braid connected to a coil, the braid may represent the distal portion and the coil may represent the proximal portion, or vice versa. Understanding this convention, as used throughout the specification and claims, attention may now be given to the following description of the various embodiments.

Figure 2:
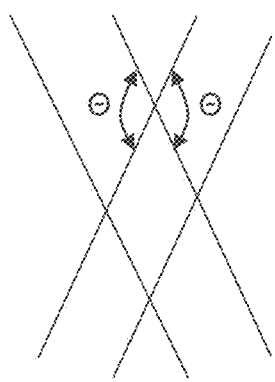
FIGS. 2-3 illustrate braid angles on a braided occlusive device.
Figure 3:
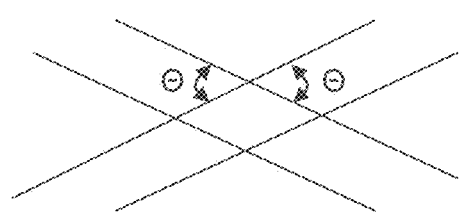

An occlusive device 10 is shown in FIG. 1. The occlusive device shown is a tubular braid. The wires comprising the braid have a circular cross section, although different cross sectional shapes (i.e. elliptical, semi-circular, rectangular, etc.) could also be used. The braid itself may have a circular cross section, although different cross sectional shapes (i.e. elliptical, semi-circular, rectangular, etc.) could also be used. Radiopaque material such as tantalum or platinum could also be used to aid imaging. In one example the device is made entirely from nitinol wires. In another example the device is a combination of nitinol and platinum wires. In another example the braid is a combination of nitinol and tantalum wires. In another example the device is made of cobalt chromium wires. In another example, various combinations therein of nitinol, platinum or tantalum, and cobalt chromium wires are used in the device. The device can be braided from the wire material combinations listed above where the diameter range of the wires is between 0.0005"-0.003". The number of wires used in the braid can range from 30-500. In one example, 96-192 wires are used in the braid. The braid angle can be between 30-150 degrees. In one example a braid angle between 68-143 degrees may be used. FIG. 2 shows an obtuse braid angle configuration while FIG. 3 shows an acute braid angle configuration. These configurations would be how the braid sits when proceeding longitudinally along the length of the occlusive device (i.e. left-to-right or right-to-left in FIG. 1). The braided occlusive device is highly adaptable in space-filling applications thus promoting folding and adaptability when deployed within an aneurysm or vessel malformation. This adaptability is due to a combination of factors including the softness of the wires used to create the braid, the ratio of wire diameter to overall braid diameter, the braid angle used, and the shape of the occlusive device. Polymer microfibers may be included within the combination of materials used in the occlusive device. Alternatively, polymer microfibers may be used alone to make the occlusive device. A biodegradable material may also be used alone, or among the combination of material used in the braid. In one example, the braid is made of three different types of wire. In such an example, the majority of the braid can be made of small diameter wire (i.e. between 0.0005"-0.002") to promote shape retention and adaptability of the braid. Tantalum wires can also be used periodically at places within the braid to promote visibility, with the added benefit that as the braid folds inwards during space-filling, the visibility will only be multiplied as the tantalum-containing portions get packed closer together. Larger diameter wires can sit on the outside of the braid, similar to a rail system where these larger wires contact the delivery device (i.e. microcatheter) during deployment, and contact the vessel wall when deployed. Since these larger wires will contact the inner surface of the microcatheter, the rest of the braid (comprising smaller wires) glides making deployment easier by reducing overall friction during delivery. Similarly, these larger wires promote expansion when deployed and create varied profile regions which the smaller braid wire portions can subsequently fill. The braid can also include hydrogel. Hydrogel generally expands on contact with a certain ph substance, such as blood, and is typically used in embolic materials such as coils. The hydrogel can be placed on the interior and/or exterior of the braid. When placed on the exterior of the braid it can fill some of the space between the braid and vessel wall. When placed within the braid it can fill some of the interior space, especially once the braid folds inward upon itself, and help maximize the space filling potential of the braid. Though various measurements are offered by way of examples to describe the braid, these measurements are not meant to limit the scope of the invention and are instead offered as examples.

Additional occlusive device embodiments utilize different shapes aside from the tubular braid configuration shown in FIG. 1. These embodiments are shown in FIGS. 4-11.

Figure 4:
FIG. 4 illustrates a cross section of a linearly tapered braided occlusive device.

One embodiment shown in FIG. 4 utilizes a linearly tapered tubular braid, where the braid diameter tapers in a linear manner from either the proximal to distal end of the braid, or vice-versa.

Figure 5:
FIG. 5 illustrates a cross section of a step tapered braided occlusive device.

Another embodiment shown in FIG. 5 utilizes a step-tapered profile shape where the braid tapers from a smaller diameter to a larger diameter in a step-wise manner. Different shapes can be used to create the step-tapered shape between the smaller and larger diameter regions, such as rectangular, elliptical, etc.

Figure 6:
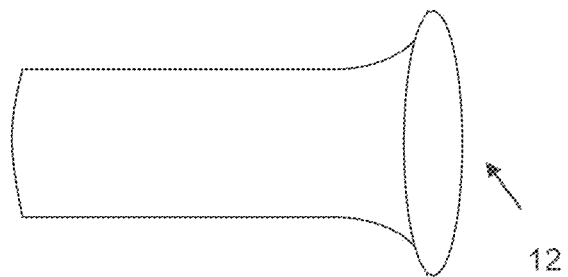
FIG. 6 illustrates a braided occlusive device with a trumpeted shape at one end.

Another embodiment shown in FIG. 6 has an enlarged, trumpeted shape 12 at either the proximal or distal end of the occlusive device.

Figure 7:
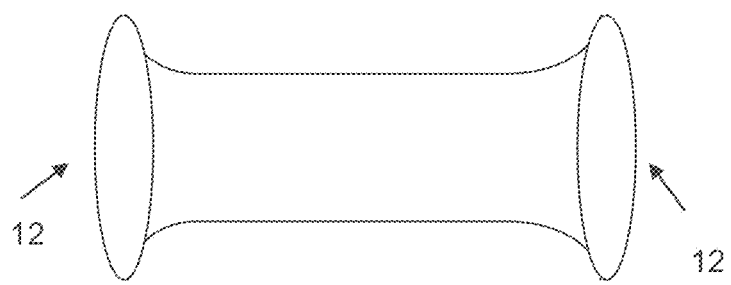
FIG. 7 illustrates a braided occlusive device with a trumpeted shape at both ends.

Another embodiment shown in FIG. 7 has an enlarged, trumpeted shape 12 at both the proximal and distal ends of the occlusive device.

Figure 8:
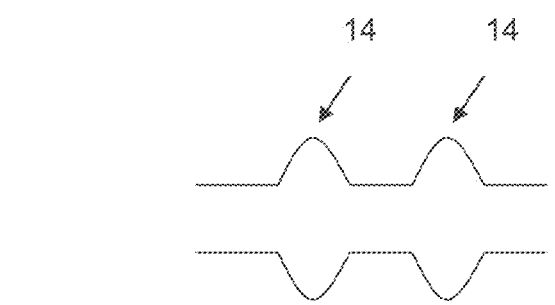
FIG. 8 illustrates a cross section of a braided occlusive device with a variable pitch.

Another embodiment shown in FIG. 8 has a variable pitch profile. Though the figure shows alternating enlarged pitch regions 14, other possibilities may include a smaller pitch followed by a larger pitch, a larger pitch followed by a smaller pitch, multiple smaller pitch regions followed by one or more larger pitch regions, multiple larger pitch regions followed by one or more smaller pitch regions, or various combinations of smaller pitch/larger pitch regions used to create a variable pitch profile through the length of the occlusive device.

Figure 9:
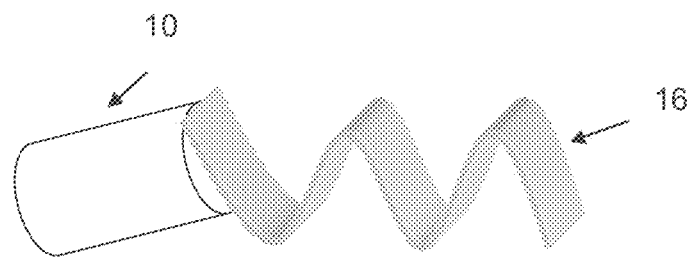
FIG. 9 illustrates an occlusive device comprising a braided structure connected to a coil shaped structure.

Another embodiment shown in FIG. 9 is an occlusive device comprising a tubular braided member 10 (similar to the tubular braided member of FIG. 1) connected to a coiled member 16. In one example of this embodiment, the distal component of the occlusive device (which is the first component inserted into the malformation or aneurysm) is tubular and the more proximal component is coiled. This allows the distal component to adapt to the dome of the aneurysm or vessel malformation, and the proximal component to coil to fill the space of the malformation. The braided member may not necessarily be tubular and can adopt one or more of the shapes shown in the other various embodiments described.

Figure 10:
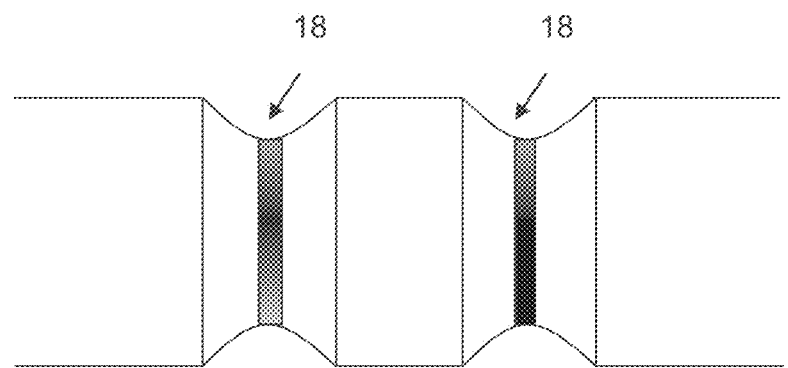
FIG. 10 illustrates a cross section of a braided occlusive device segmented by radiopaque markers.

Another embodiment shown in FIG. 10 is an occlusive device utilizing crimped radiopaque marker bands 18. Marker bands 18 are crimped along particular regions of the occlusive device to create smaller diameter regions to vary the shape of the occlusive device. The marker bands also allow for enhanced imaging of the device during deployment due to the radiopaque material quality. The marker bands may have variable spacing to change the folding and adaptability of the occlusive device as it is deployed in the aneurysm or malformation.

Figure 11:
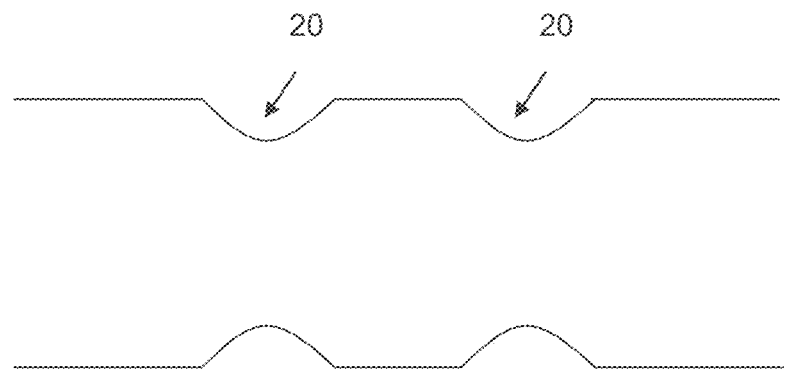
FIG. 11 illustrates a cross section of a braided occlusive device which is electropolished at various areas along its length to provide variable wall thickness.

Another embodiment shown in FIG. 11 is an occlusive device utilizing electropolished regions. Certain regions of the occlusive device are electropolished to create smaller wall thickness regions 20 to optimize folding, inverting and shape retention of the braid inside the aneurysm or malformation. In one example, a distal portion of the occlusive device is selectively electropolished along particular regions to increase the folding, inverting, and shape retention of the braided occlusive device within the dome of the aneurysm or malformation. In this particular example the more proximal portion of the device does not utilize eletropolishing, and thus has a larger wall thickness to promote more uniform space filling at the base of the aneurysm or malformation.

Figure 12:
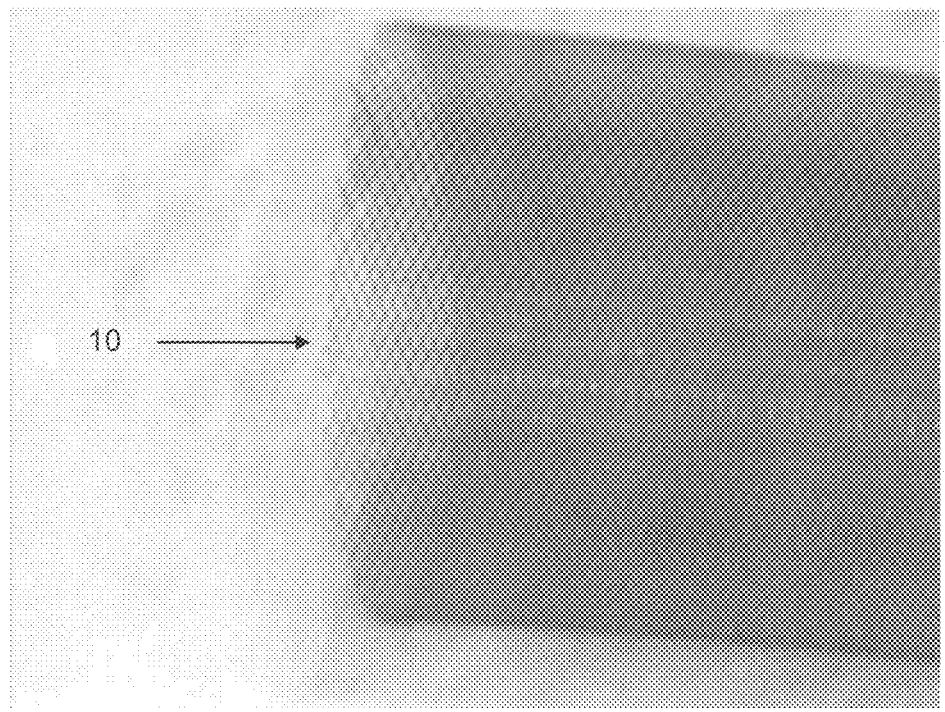
FIG. 12 illustrates a straight tubular braided occlusive device which may be deployed in an aneurysm model.
Figure 13:
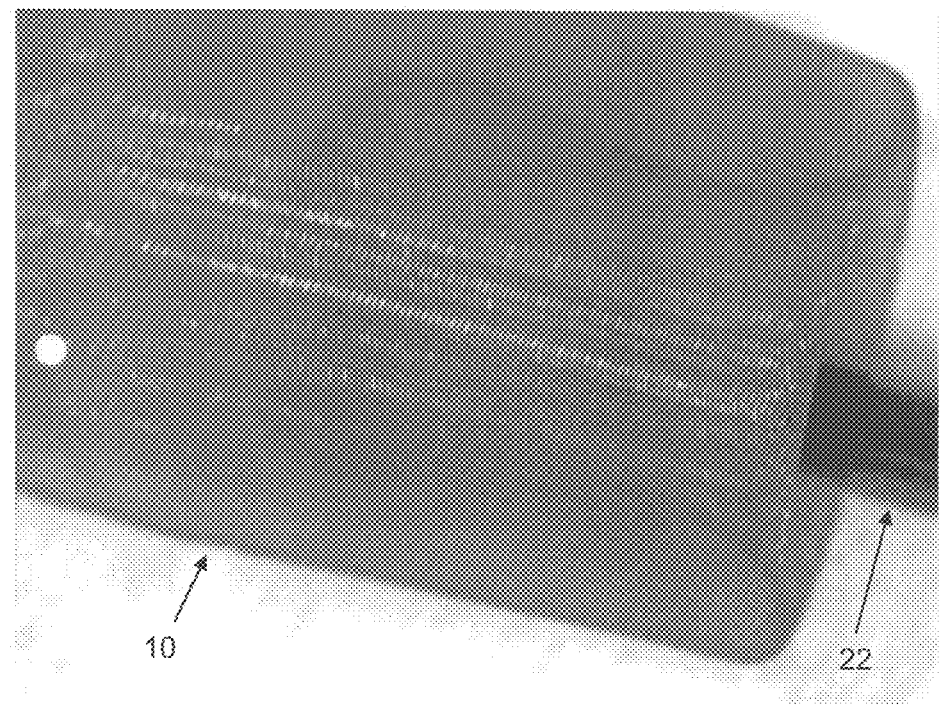
FIG. 13 illustrates the occlusive device of FIG. 12 folded in upon itself during deployment.

FIG. 12 shows a tubular braid occlusive device similar to the embodiment shown in FIG. 1. The occlusive device is highly conformable and adaptable in shape. FIG. 13 shows the tubular braid occlusive device 10 delivered through a delivery device (i.e. a microcatheter) 22. As shown in FIG. 13, the device can fold in upon itself due to the shape and material properties of the tubular braid.

Figure 14:
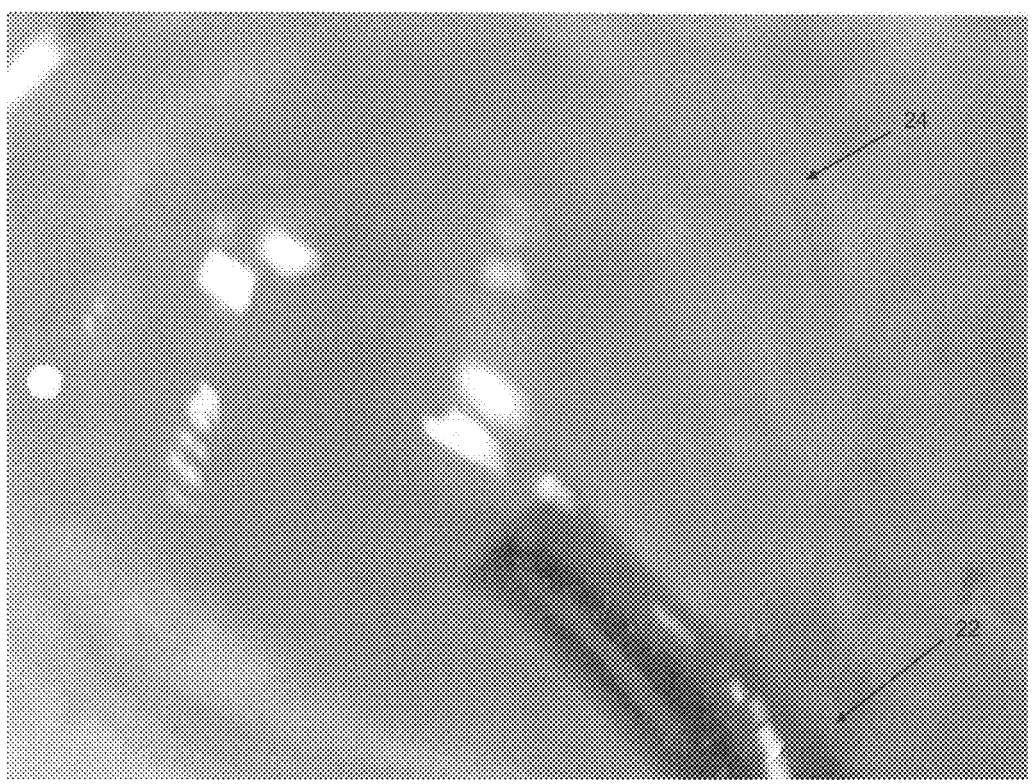
FIG. 14-21 illustrate the deployment of the occlusive device of FIG. 12 in an aneurysm model.
Figure 15:
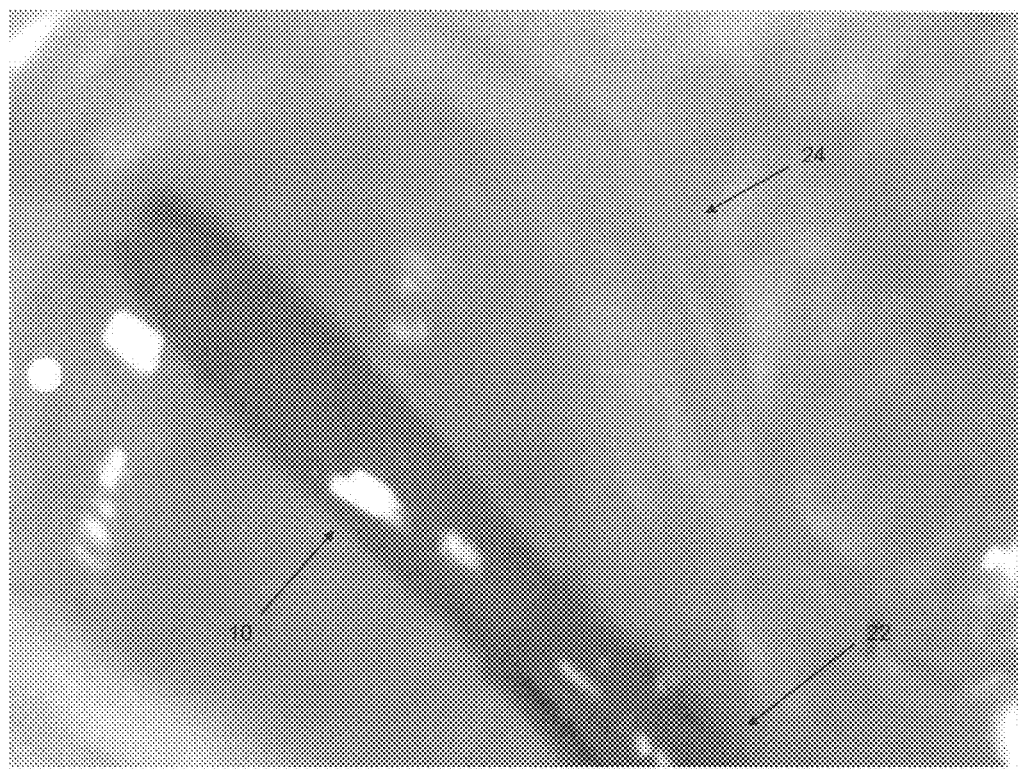
Figure 16:
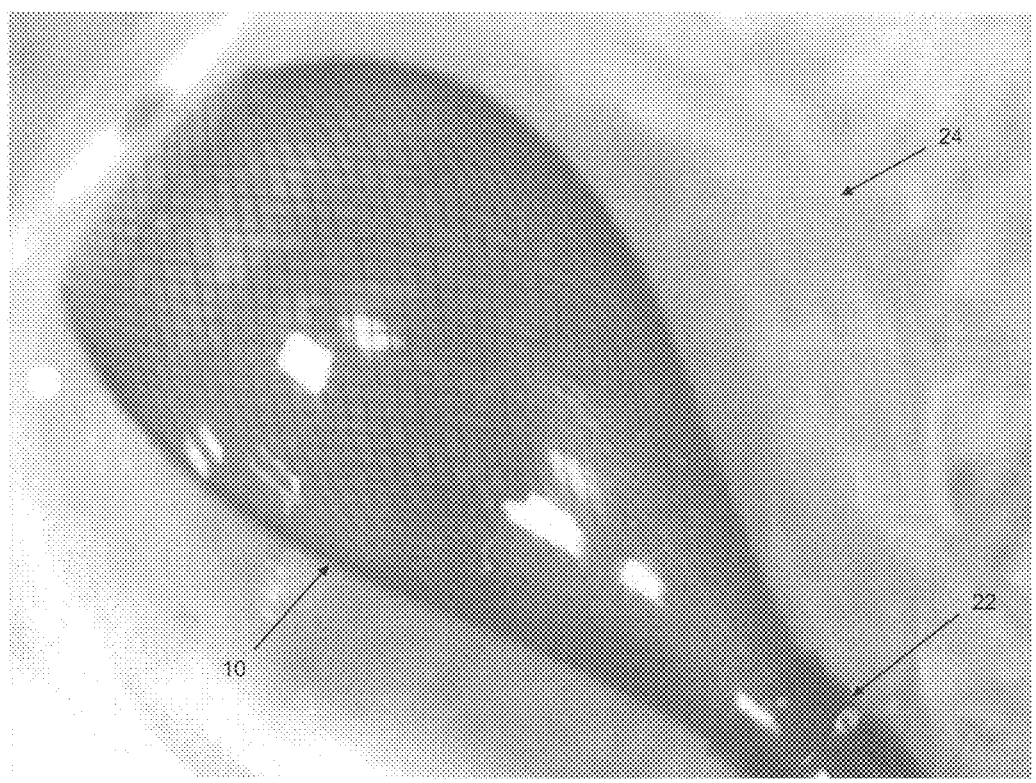
Figure 17:
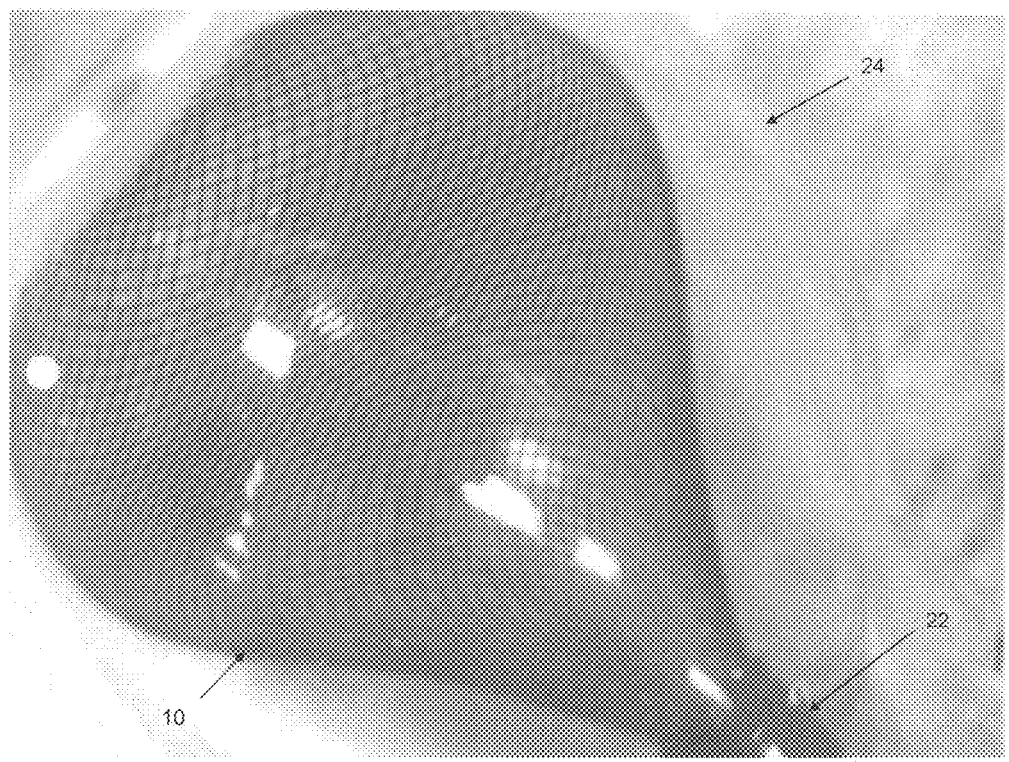
Figure 18:
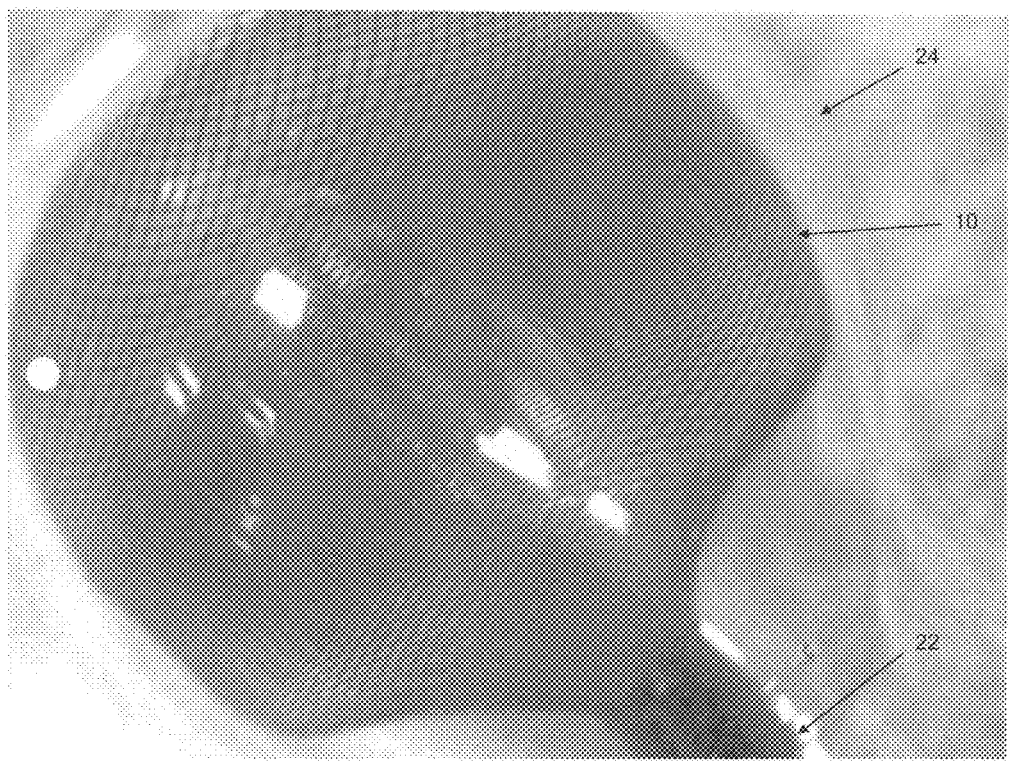
Figure 19:
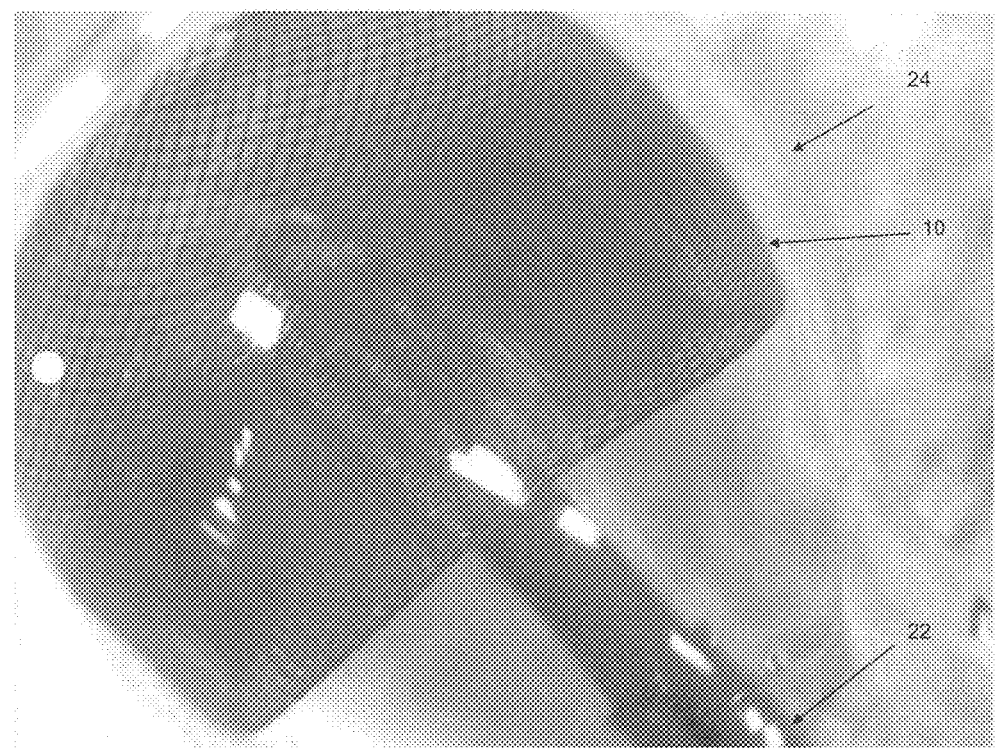
Figure 20:
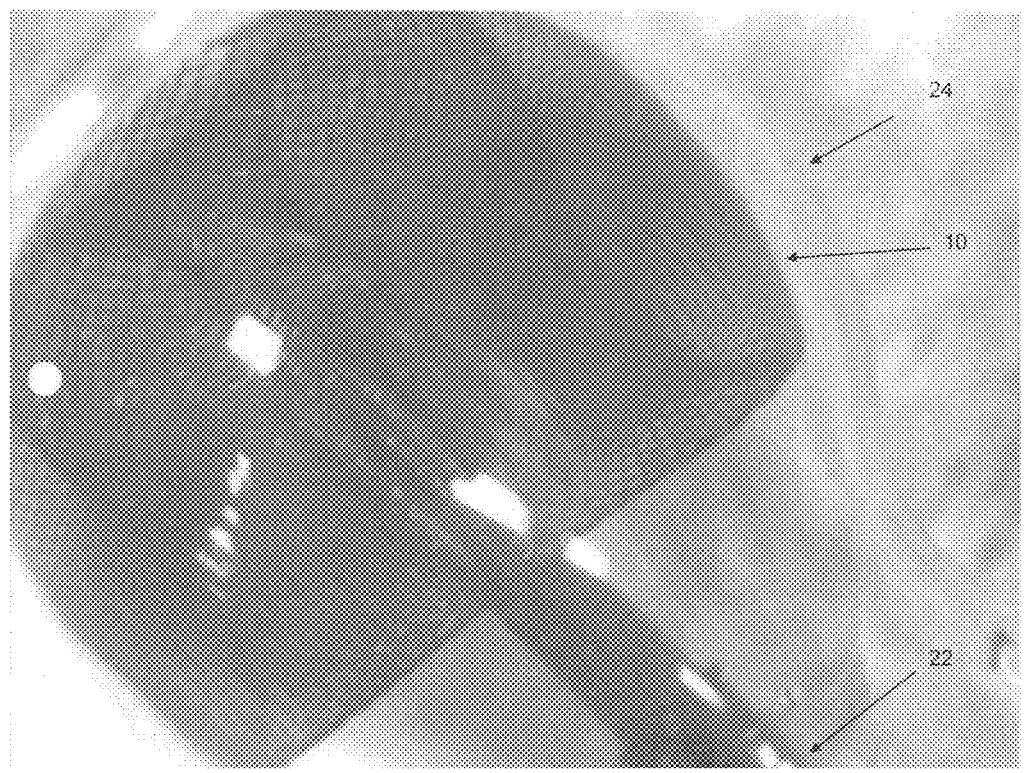
Figure 21:
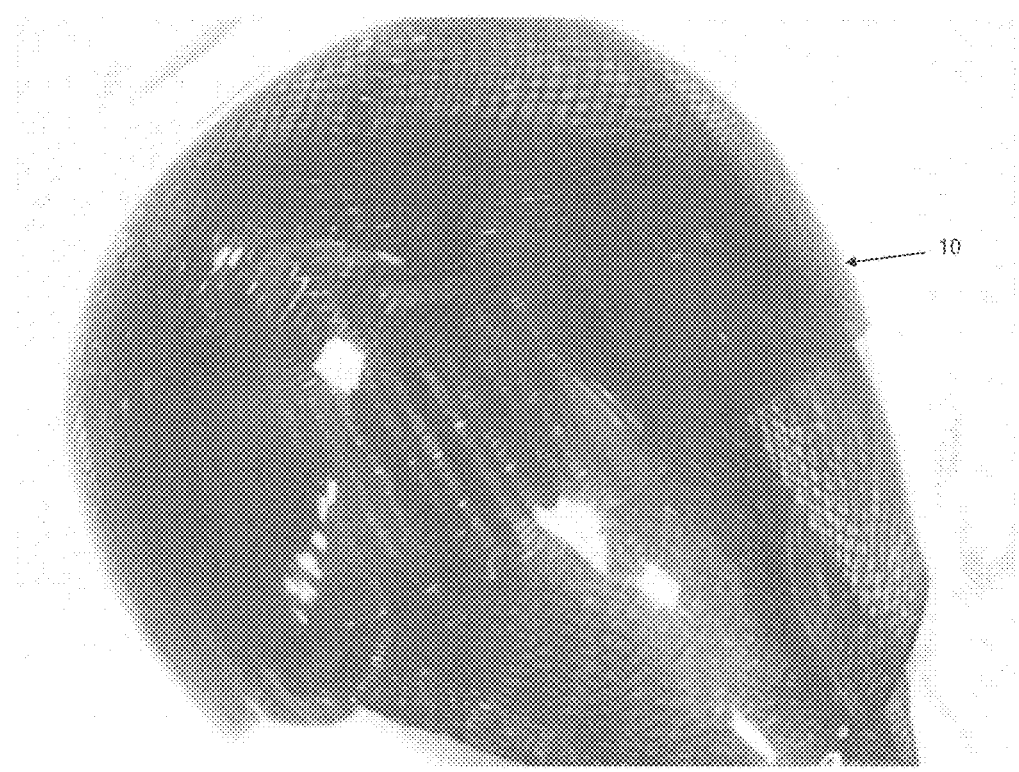

FIG. 14 shows an aneurysm model 24 with a delivery device 22 used to deliver the occlusive device within aneurysm model 24. The occlusive device 10 is pushed through the distal end of delivery device 22 and initially adopts a contracted state similar to the diameter of the delivery device 22, as shown in FIG. 15. Eventually the occlusive device starts adapting to the shape of the aneurysm as shown in FIGS. 16-18. Due to the shape adaptability of the braid used to create the occlusive device, the device will then start folding in on itself, thus maximizing its space filling potential, as shown in FIGS. 19-20. Once the braid folds in upon itself to fill the empty portion within the deployed braid, it will then expand to fill the rest of the aneurysm, as shown in FIG. 21.

Figure 22:
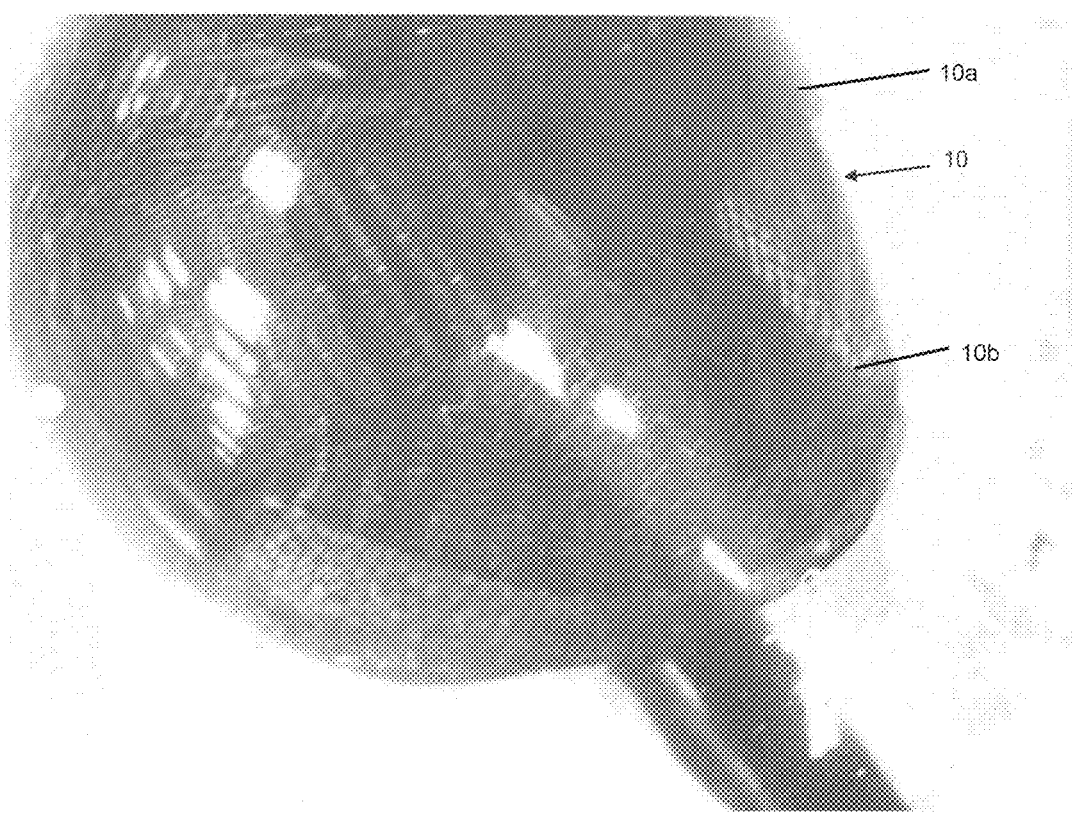
FIG. 22 illustrates two occlusive devices deployed in an aneurysm model.

FIG. 22 shows two sequentially deployed occlusive devices 10a and 10b which can be used to form to fill an aneurysm model. The occlusive devices 10a and 10b may separately be deployed one after the other, or the two occlusive devices may be connected together to create an extended length occlusive device 10. In either case the device 10a delivered first is considered the distal portion and the device delivered second 10b is considered the proximal portion. An arrangement involving multiple occlusive devices may be useful in a particularly large aneurysm or malformation.

Figure 23:
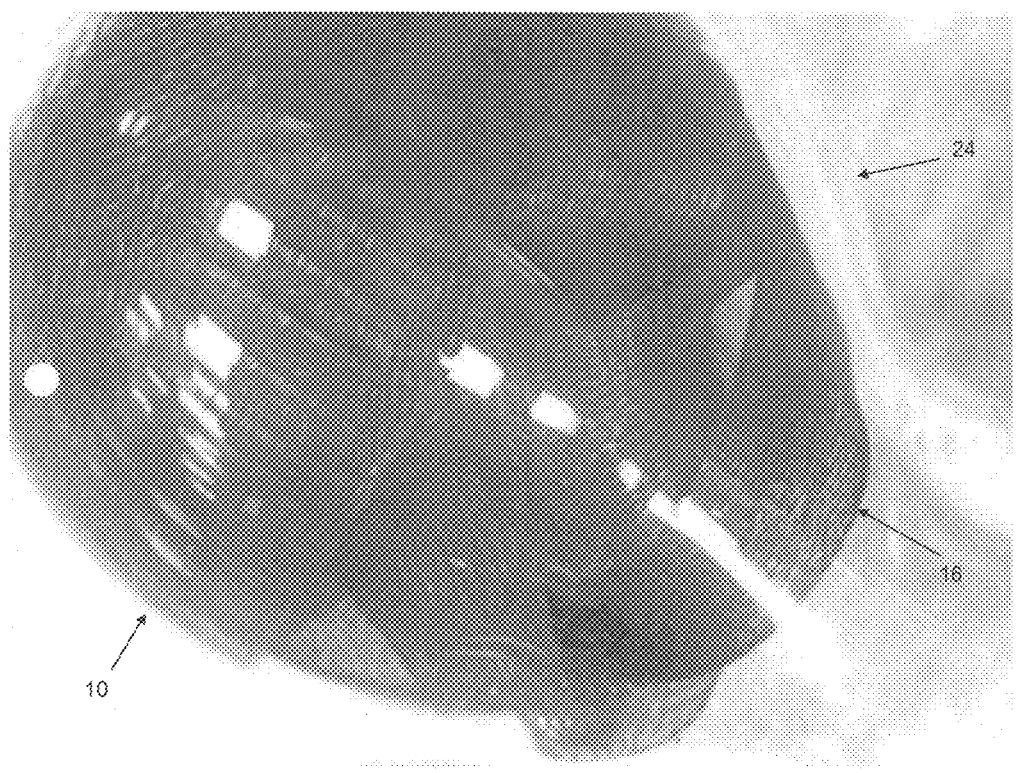
FIG. 23 illustrates an occlusive device utilizing a distal tubular and proximal coil structure in an aneurysm model.

FIG. 23 shows the device of FIG. 9 deployed in an aneurysm model 24. The occlusive device has a distal portion that is a tubular braid component 10 and a proximal portion that is a connected coiled component 16. Another example may utilize a tubular braid component 10 and a separately deployed coiled component 16. Another example may utilize a braid component of a non-tubular shape (i.e. the shapes in FIG. 4-8, 10 or 11) and a coiled component 16. In this figure the braid component 10 sits distal to the coiled component 16 and is deployed first within the aneurysm. The braid adapts to the shape of the aneurysm dome and folds in upon itself to maximize space filling, as highlighted earlier in FIGS. 15-20. The coiled component 16 then fills in the base of the aneurysm or malformation. Another example may utilize a distal coiled component and a proximal braid component. Another example may utilize one or more braid components separated by one or more coiled components.

Figure 24:
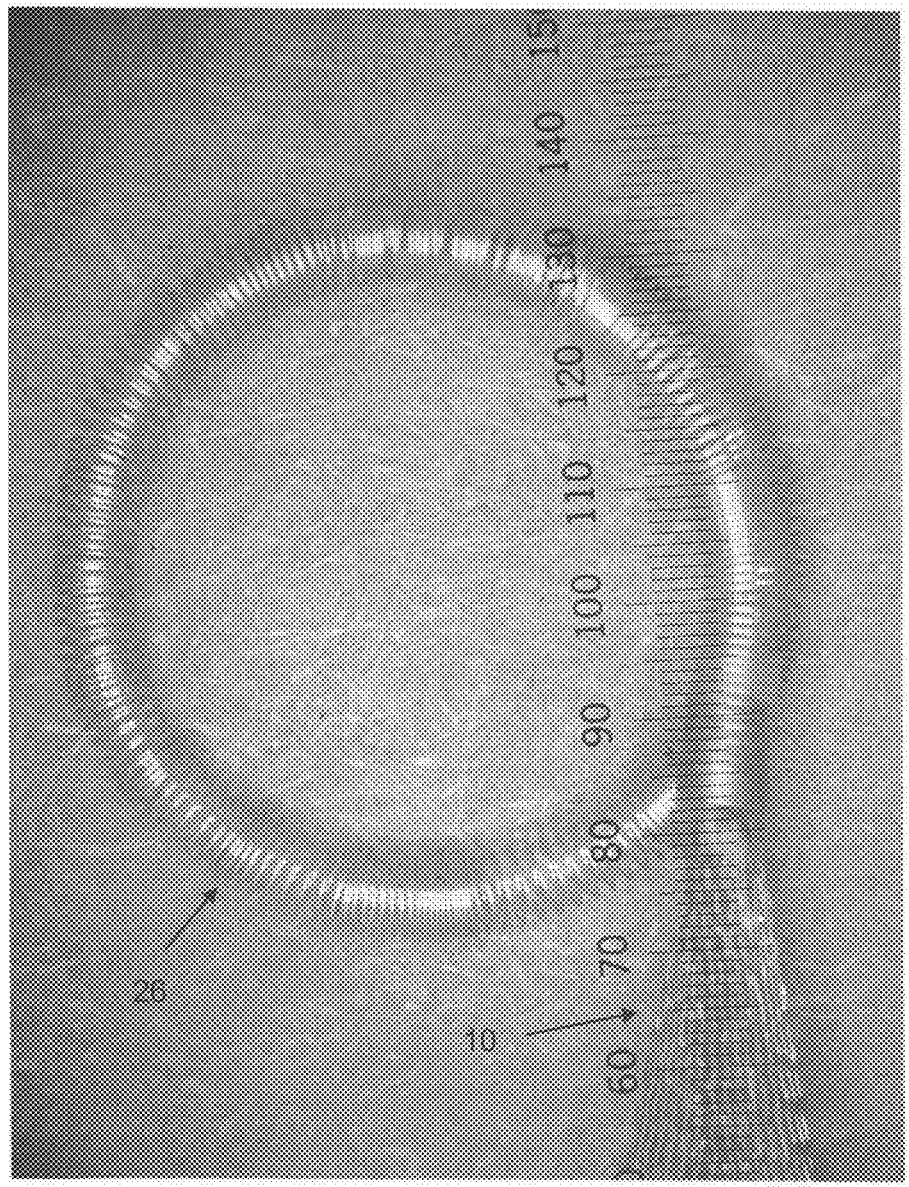
FIGS. 24-25 illustrate an braided occlusive device connected to a coil.
Figure 25:
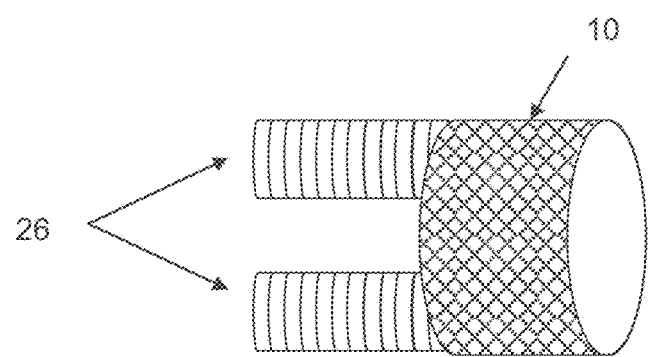

In another embodiment shown in FIGS. 24-25 the braided occlusive device 10 may be attached to one or more coils 26. As indicated in FIG. 24, the braid may be packed into one end of the coil. Alternatively, one or more coils may be attached around the periphery of the braided occlusive device. Alternatively, one or more coils may be attached within the braided occlusive device, as shown in FIG. 25. In one example, the one or more coils are attached to the distal end of the braided occlusive device, such that the coil is deployed first. When used to fill a malformation such as aneurysm, the coil will create a boundary around the dome of the aneurysm which the braid will subsequently fill.

In another embodiment the braided occlusive device is connected to one or more coils, where said coils are embolic coils. The coils 26 shown in FIGS. 24-25 may be embolic coils. Embolic coils are often used to treat vascular malformations such as aneurysms by filling the malformation. In one example, the one or more embolic coils are attached to the distal end of the braided occlusive device, such that the coil is deployed first. When used to fill a malformation such as aneurysm, the coil will create a boundary around the dome of the aneurysm which the braid will subsequently fill.

The braided occlusive device can be used with other embolic material as well to fill aneurysms or other vascular malformations. For example, a braided occlusive device can initially be deployed to conform to the shape of the aneurysm while a hydrogel is subsequently deployed to fill the space within the aneurysm. Alternatively, one or more embolic coils can initially be implanted and a braided occlusive device is subsequently implanted to fill the aneurysm. Alternatively still, a braided occlusive device is initially implanted and one or more embolic coils are subsequently implanted to fill the aneurysm. In one example, the one or more embolic coils can utilize hydrogel. Various combinations of the occlusive device, embolic agents (such as coils, liquid embolic, plugs, etc) and hydrogel are feasible as well.

The delivery system for the occlusive device comprises a pusher 28 which is connected to a portion of the occlusive device. In one embodiment pusher 28 is a metallic core wire. The core wire has a combination of high tensile strength and flexibility to aid in trackability. The core wire could be a solid shaft, a coil, or a braided wire. It can be radiopaque or may include radiopaque components in order to aid in imaging during deployment. In one example, the core wire is a coil or shaft between 0.003-0.006" outer diameter and is made of tantalum or platinum. The coil or micro-coil wound configuration of the core wire would allow for more flexibility versus the more rigid shaft which would have higher tensile strength. An example of the coil is nitinol and/or stainless steel material coil spring. Another example is tantalum and/or platinum coil spring. An example of the braided wire or microbraid includes three platinum or tantalum wires of 0.0005"-0.002" diameter wound together. Another example includes three nitinol or stainless steel wires of 0.0005"-0.0002" diameter wound together. Nitinol and/or stainless could be used with tantalum and/or platinum to promote visualization. Though various measurements are offered by way of examples to describe the pusher, these measurements are not meant to limit the scope of the invention and are instead offered as examples.

In another embodiment pusher 28 is an elastic member. The elastic may be formed of a polymer, such as polyblend or other elastic polymers, and may include radiopaque material to aid in imaging.

The pusher could also be a combination of an elastic and metallic material.

Detachment means could be incorporated on the proximal and/or distal portion of the pusher, depending on where the pusher mates with the braid. Examples include electrolytic, thermal, or mechanical detachment means. One such thermal detachment that could be used is shown in U.S. Pat. No. 8,182,506 and U.S.20060200192, which are hereby incorporated by reference in their entirety.

An elastic, spring, or stretch-resistant element—such as Engage®, a polymer made by Dow Chemical, could be attached to the distal and/or proximal end of the pusher. The utilization of such an element would be especially useful for a thermal detachment design where a polymeric material could be severed when a sufficient temperature is reached. In one example this element acts as a detachment junction, which can be degraded, severed, or mechanically manipulated to detach the occlusive device from the pusher.

The distal end of the pusher can be attached to the braid by a fused polymeric Material—such as an Engage—acting as an intermediary between the pusher and braid. The fused polymer can be disengaged by electrolytic or thermal means. Alternatively, the distal end of the pusher can be crimped into a radiopaque (i.e. platinum) marker and electrolytic detachment can be used at a point proximal or distal of this marker. Alternatively, a mechanical screw detachment system may be used where the distal end of the pusher physically screws into, and out of, a corresponding receiving member on the braid. Alternatively, a thermal detachment system can be used where the pusher/braid junction utilizes a material that can be thermally disintegrated to initiate detachment.

Another electrolytic detachment system utilizes a wire (i.e. one made of stainless steel) running under a platinum or tantalum shaft or coil. The stainless steel underwire can be electrolytically degraded to separate the braid and the pusher.

In another embodiment pusher 28 is a hypotube. The hypotube may be formed of a metallic material (such as nitinol and/or stainless steel), radiopaque material (such as palladium and/or tantalum), a polymer, or combinations therein. Occlusive device 10 is attached at the distal end of the hypotube, and may be connected to the hypotube by a detachment junction which is severed or manipulated to affect separation between the hypotube and occlusive device. A stylet may be included within the hypotube to provide greater column strength to the hypotube, especially during tracking through the delivery device (i.e. microcatheter) and vasculature. This stylet may be removable. In one example the hypotube is delivered through the delivery device (i.e. microcatheter) to a particular site within the vasculature. The stylet is subsequently removed by retracting the proximal end of said stylet. The hypotube may be formed of nitinol or stainless steel, and may include radiopaque agents (such as tantalum or palladium) to aid in imaging. The distal end of the hypotube may utilize a coil to aid in flexibility of the distal end of the hypotube. A polymer (i.e. PTFE or Teflon) may be used as an interior liner through the distal coiled portion of the hypotube to prevent leaks of any substances that may be delivered through the hypotube.

In one example hypotube pusher 28 is used to deliver occlusive device 10 to a particular region within the vasculature. Following detachment of the occlusive device, the hypotube is subsequently used to deliver further embolic agents (i.e. embolic coils, liquid embolic, hydrogel). In the example of an aneurysm, occlusive device 10 would be used to conform to the general shape and fill some of the aneurysm while the additional embolic agents delivered through the hypotube pusher would fill the remaining portion of the aneurysm. Since the hypotube is already within the delivery device (i.e. microcatheter), delivery time would be significantly reduced since one could use the hypotube to deliver additional agents instead of removing the hypotube completely and using the microcatheter for further embolic agent delivery.

Figure 29:
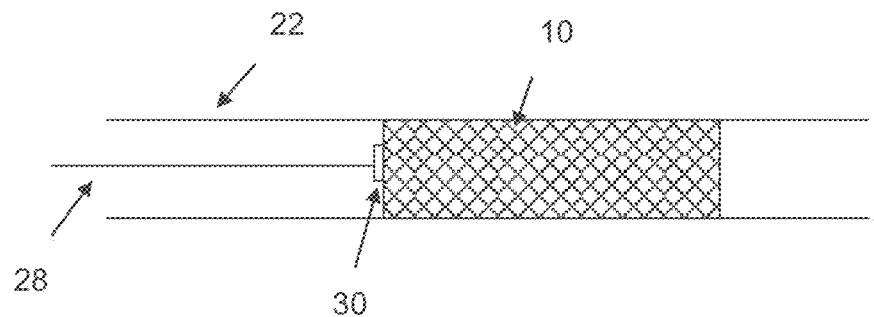
FIGS. 29-32 illustrate various delivery configurations for a braided occlusive device.

Multiple occlusive device delivery configuration embodiments are contemplated. In one embodiment shown in FIG. 29, a pusher 28 is attached to the proximal end of the occlusive device 10, and the occlusive device is positioned and delivered linearly (i.e. said occlusive device is not substantially inverted or flipped). A detachment junction 30 may be present where thermal, electrolytic, or mechanical means may be utilized to sever the pusher from the occlusive device.

Figure 30:
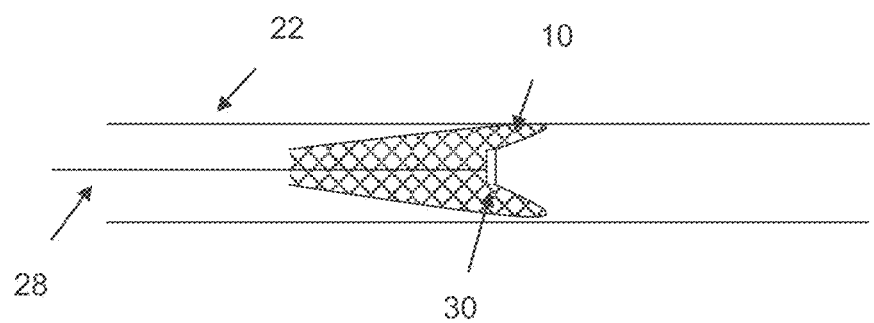

In another embodiment shown in FIG. 30, the pusher is attached to a portion of the occlusive device 10, and the occlusive device is folded or inverted around the pusher within the delivery device. A detachment junction 30 may be present where thermal, electrolytic, or mechanical means may be utilized to sever the pusher from the occlusive device.

Figure 31:
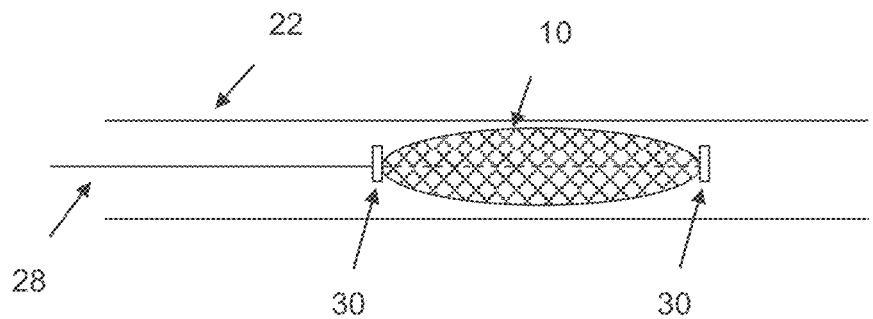
Figure 32:
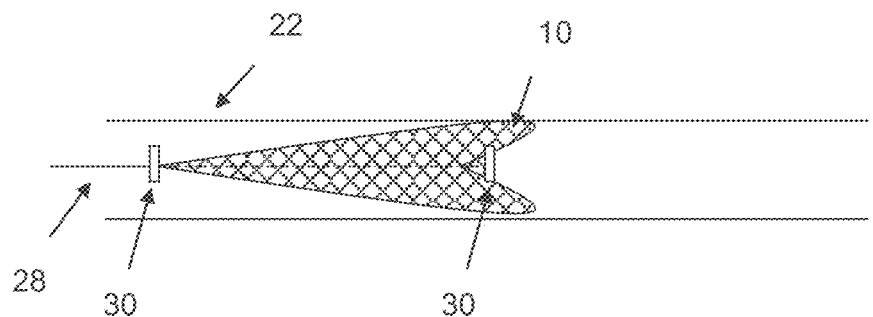

In another embodiment shown in FIG. 31 the occlusive device is connected to the pusher at a proximal and distal location. In another embodiment shown in FIG. 32, the pusher is attached to a portion of the braid and the braid is folded or inverted around the core wire and connected to the core wire at another, more proximal location. A detachment junction 30 can be included at the more proximal location, the more distal location, or both locations to sever the occlusive device 10 from the pusher 28. These embodiments would be particularly useful for the elastic pusher or spring core wire pusher concepts where the tension of the wire could be helpful in aiding adaptability of the braid by transferring the stored tension to the braid during placement of said braid. The elastic or spring pusher could be pulled into tension when placed in the delivery device (i.e. microcatheter). The reduced inner diameter of the delivery device keeps the occlusive device in a reduced profile state, thus retaining the tension on the pusher. As the occlusive device is released from the delivery device and placed in the vessel, the occlusive device adopts its expanded configuration and the tension is transferred from the pusher to the braid as the braid encounters an opposing force (i.e. from the aneurysm dome wall, or the blood vessel wall). This tension transfer aids in the folding of the compliant occlusive device, thus aiding its adaptability within the vessel, aneurysm or malformation. In one example, the detachment junction is located on the more proximal location of the pusher, resulting in a more distal portion of the pusher being severed during detachment. The more distal elastic pusher component when detached could subsequently remain within the vessel as another space filling material, along with the braid.

Though FIGS. 29-32 show one or two detachment junctions, more junctions may be utilized.

Figure 26:
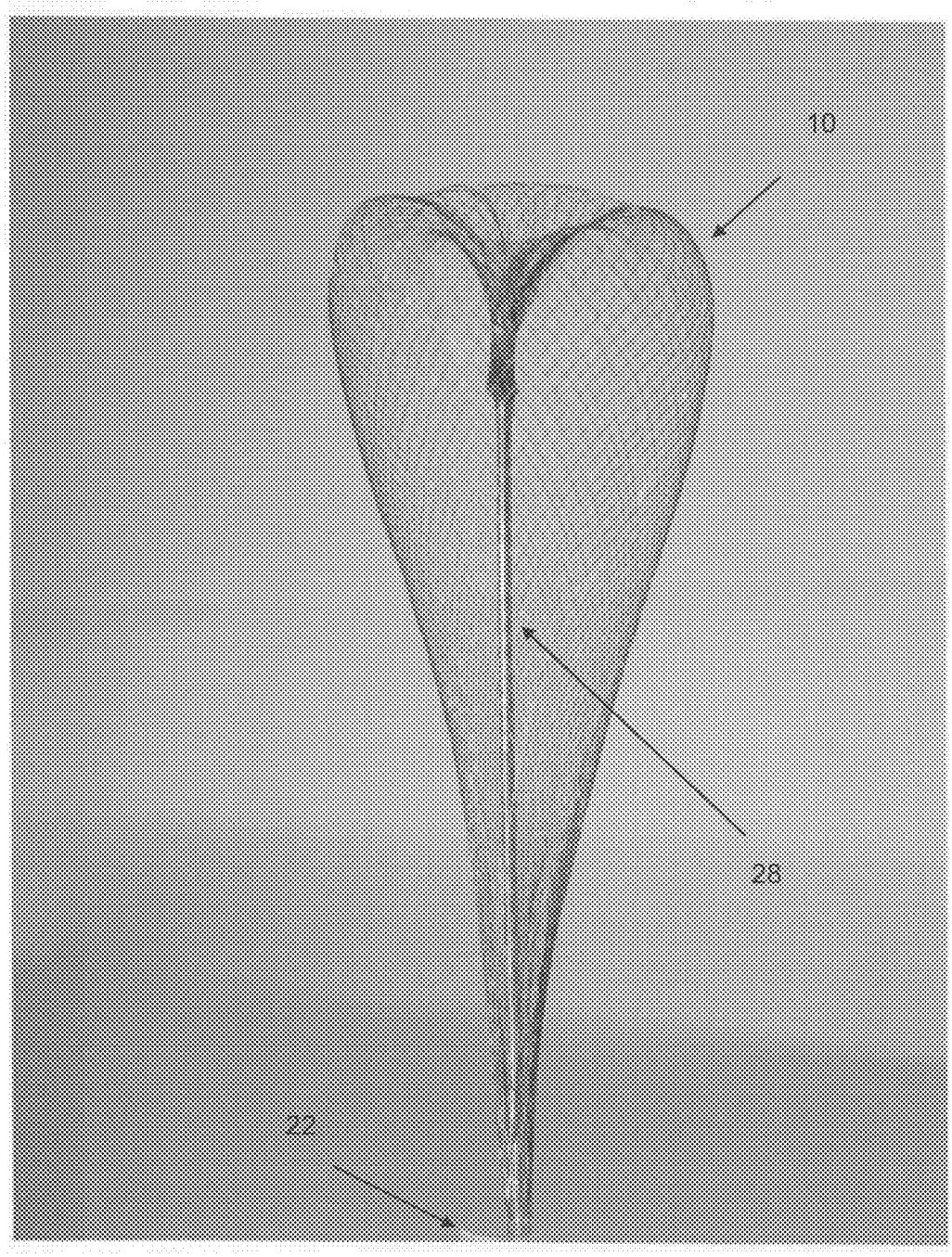
FIGS. 26-28 illustrate a braided occlusive device delivered in an inverted configuration.
Figure 27:
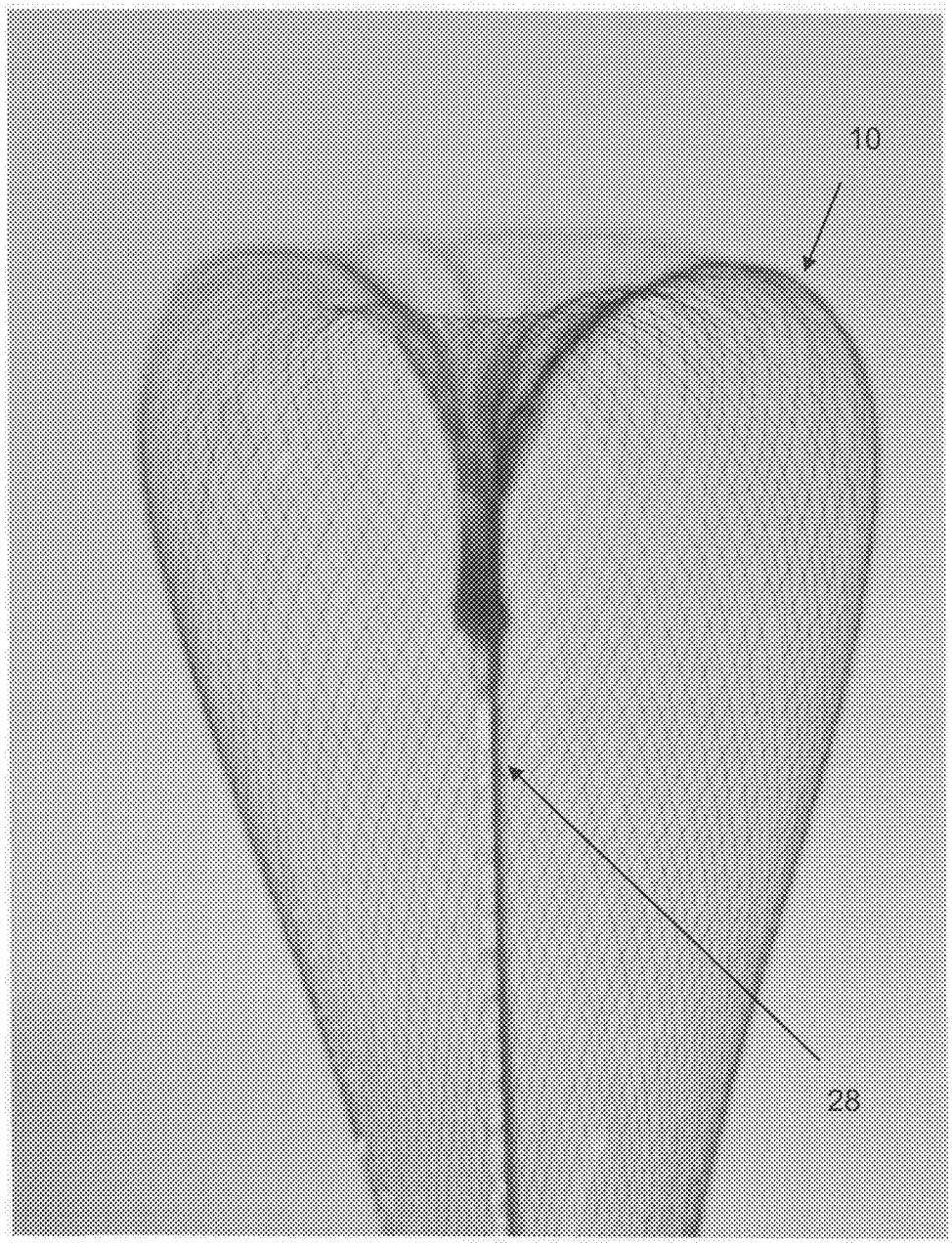
Figure 28:
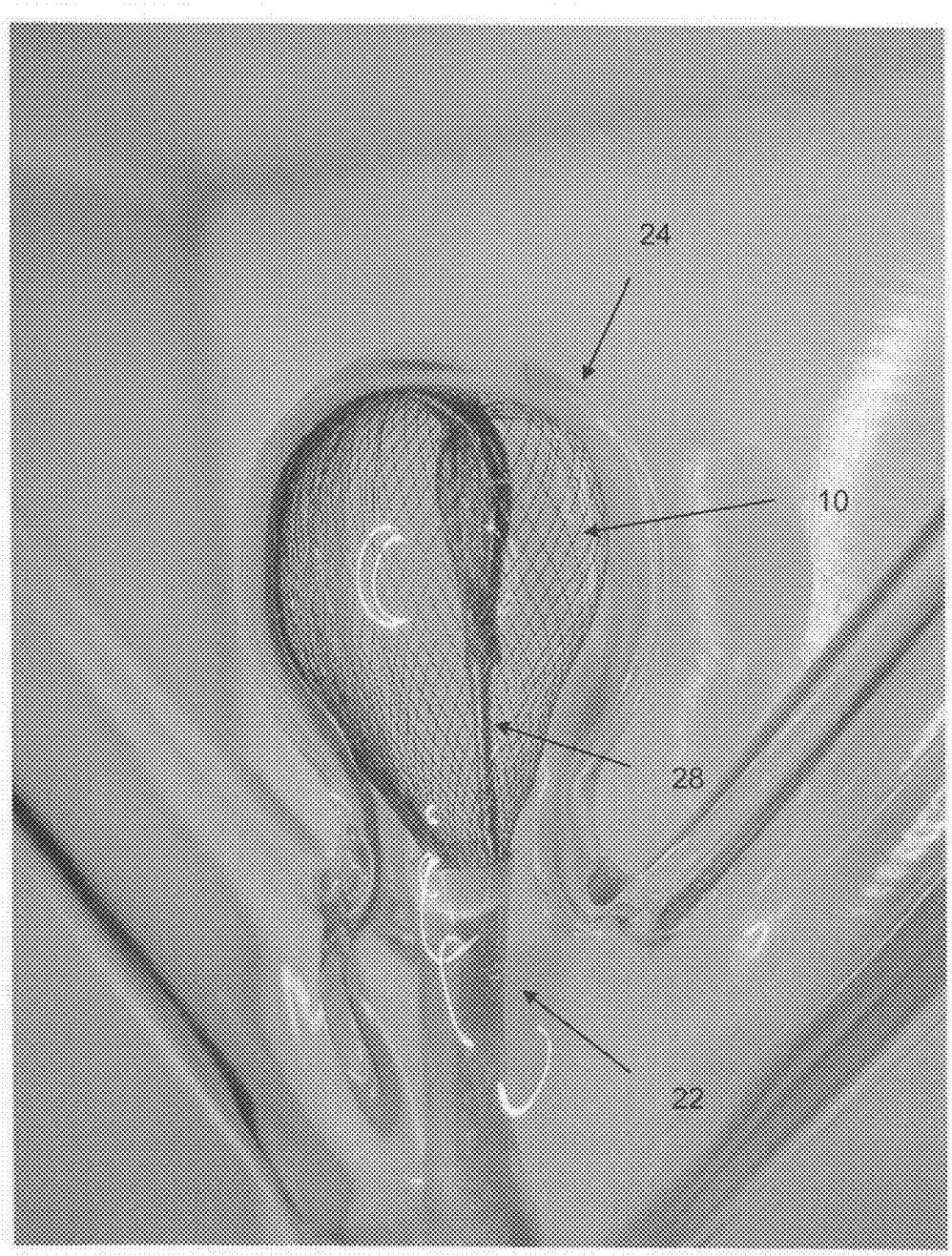

In one example shown in FIGS. 26-28, the folded or inverted shape of the occlusive device 10 about pusher 28 results in a fountain-like shape at the distal end of occlusive device 10. The figures show the occlusive device when in a deployed (i.e. outside of delivery device 22) shape. FIG. 28 shows the occlusive device within an aneurysm model 24. Where the braid is used to fill an aneurysm, the portion of the braid contacting the dome of the aneurysm will have the structural support of the pusher immediately behind, thus promoting a higher engaging force between the braid and the dome wall, resulting in a better retention force between the braid and aneurysm wall. The bulbous portion of the fountain shape engages the aneurysm wall while the in-folded portion (see FIGS. 26-28) connected to the pusher allows an easier fill path for subsequent portions of the braid as they are delivered from the delivery device. In one example, certain wires at the distal portion of the braid are heat treated to augment this fountain shape. The braid first conforms to the shape of the aneurysm while subsequent portions of the braid pack the interior of the aneurysm.

What is claimed is:

1. A device for filling and occluding a vascular malformation comprising:
    a distal portion, having a distal end inwardly inverted on itself, and configured to expand and conform to an interior surface of a vascular malformation; and,
    a proximal portion that is connected to the distal portion and is radially collapsed and becomes folded and coiled into the distal portion to substantially fill a remaining interior volume of the distal portion after said distal portion is deployed therein;
    wherein at least one of said distal portion and said proximal portion is a tubular braid.

2. The device of claim 1 wherein said tubular braid comprises wires braided to form a braid angle of between 30 and 150 degrees.

3. The device of claim 2 wherein said tubular braid comprises wires braided to form a braid angle of between 68 and 143 degrees.

4. The device of claim 1 wherein said tubular braid comprises a plurality of wires.

5. The device of claim 4 wherein said tubular braid further comprises hydrogel.

6. The device of claim 1 wherein said tubular braid comprises a shape selected from the group consisting of cylinder, linearly tapered, step-tapered, rectangular, elliptical, trumpeted, bulbous, and variable pitch.

7. The device of claim 1 wherein one of said distal portion and said proximal portion comprises at least one coil.

8. The device of claim 1 further comprising electropolished regions.

9. The device of claim 1 wherein said tubular braid comprises a shape and material selected to fold in upon itself when delivered into the vascular malformation.

10. An apparatus for occluding a vascular malformation comprising: a delivery system including:
    a sheath;
    a pusher slidably disposed within said sheath;
    an implant carried by said delivery system, said implant including:
    a distal portion configured to expand and conform to an interior surface of a vascular malformation and having a distal end inwardly inverted on itself; and,
    a proximal portion that is connected to the distal portion and is radially collapsed and becomes folded and coiled into the distal portion to substantially fill a remaining interior volume of the distal portion after said distal portion is deployed therein;
    wherein at least one of said distal portion and said proximal portion is a tubular braid.

11. The apparatus of claim 10 wherein one of said distal portion and said proximal portion comprises at least one coil.

12. The apparatus of claim 10 wherein said tubular braid comprises a shape and material selected to fold in upon itself when delivered into the vascular malformation.

13. The apparatus of claim 10 wherein said pusher comprises a core wire.

14. The apparatus of claim 10 wherein said pusher comprises an elastic member.

15. The apparatus of claim 10 wherein said delivery system further comprises a detachment mechanism.

16. The apparatus of claim 10 wherein said pusher comprises a hypotube and wherein said apparatus further comprises an embolic agent deliverable to said vascular malformation through said hypotube.

* * * * *